United States Patent [19]
Mackenzie

[11] Patent Number: 6,019,777
[45] Date of Patent: Feb. 1, 2000

[54] CATHETER AND METHOD FOR A STENT DELIVERY SYSTEM

[75] Inventor: Andrew James Mackenzie, Santa Clara, Calif.

[73] Assignee: Advanced Cardiovascular Systems, Inc., Santa Clara, Calif.

[21] Appl. No.: 08/840,495

[22] Filed: Apr. 21, 1997

[51] Int. Cl.$^7$ ................................................. A61M 29/00
[52] U.S. Cl. ........................... 606/198; 606/194; 604/96
[58] Field of Search ................................ 606/1, 108, 191, 606/194, 195, 198, 200; 623/1, 12

[56] References Cited

U.S. PATENT DOCUMENTS

| | | |
|---|---|---|
| 3,105,492 | 10/1963 | Jeckel . |
| 3,657,744 | 4/1972 | Ersek . |
| 3,868,956 | 3/1975 | Alfidi et al. . |

(List continued on next page.)

FOREIGN PATENT DOCUMENTS

| | | |
|---|---|---|
| 0 380 227 A2 | 8/1990 | European Pat. Off. . |
| 0428479 | 5/1991 | European Pat. Off. . |
| 36 40 745 | 6/1987 | Germany . |
| 57-89859 | 6/1982 | Japan . |
| 09084880 | 3/1997 | Japan . |
| 2 135 585 | 9/1984 | United Kingdom . |
| WO-A-89/01798 | 3/1989 | WIPO . |
| WO-A-89/08433 | 9/1989 | WIPO . |
| WO 95/11721 | 5/1995 | WIPO . |

OTHER PUBLICATIONS

Dotter, Charles T., Transluminally Placed Coilspring Endarterial Tube Grafts, *Investigative Radiololgy*, pp. 329–332, Sep. 10, 1969.

Dotter, Charles T., Transluminal Expandable Nitinol Coil Stent Grafting: Preliminary Report, *Radiology Journal*, pp. 259–260, Apr. 1983.

Cragg, et al., Non–Surgical Placement of Arterial Endoprostheses: A New Technique Using Nitinol Wire, *Radiology Journal*, pp. 261–263, Apr. 1983.

Maass, et al., Radiological Follow–Up of Transluminally Inserted Vascular Endoprostheses: An Experimental Study Using Expanding Spirals, *Radiology Journal*, pp. 659–663, 1984.

Wright, et al., Percutaneous Endovascular Stents: An Experimental Evaluation, *Radiology Journal*, pp. 69–72, 1985.

C.R. Bard, PE Plus Peripheral Balloon Dilatation Catheter, CR Bard Inc., Aug. 1985.

*Primary Examiner*—Michael Buiz
*Assistant Examiner*—William W. Lewis
*Attorney, Agent, or Firm*—Fulwider Patton Lee & Utecht, LLP

[57] ABSTRACT

An apparatus and method for deploying one or more stents within a body lumen comprises a catheter (such as a dilatation catheter) having a detachable proximal portion. Detaching the proximal portion from the catheter shaft allows a substantially tubular sheath to be slidably received over the proximal end of the catheter shaft. The tubular sheath has one or more substantially tubular stents positioned in a delivery configuration over a distal portion of the sheath. The sheath preferably has a proximal portion that is resistant to compressive forces, so that a user may advance the sheath along the catheter by pushing the sheath proximal end, thereby positioning the stent or stents at a desired deployment location within the body lumen. With the stents in position, the catheter proximal portion can be attached to the catheter shaft, and the stents can be deployed at the desired position. After the stents have been deployed, the catheter proximal hub can be removed, the first sheath slidably removed from the catheter shaft, a second sheath (containing additional stents) slidably introduced over the catheter shaft, the catheter proximal hub reattached, and the additional stents deployed. Thus, multiple stents can be deployed without necessitating removal of the catheter shaft until the procedure is completed.

8 Claims, 11 Drawing Sheets

U.S. PATENT DOCUMENTS

| | | |
|---|---|---|
| 3,993,078 | 11/1976 | Bergentz et al. . |
| 4,130,904 | 12/1978 | Whalen . |
| 4,140,126 | 2/1979 | Choudhury . |
| 4,159,719 | 7/1979 | Haerr . |
| 4,187,848 | 2/1980 | Taylor . |
| 4,332,254 | 6/1982 | Lindquist . |
| 4,439,185 | 3/1984 | Lundquist . |
| 4,468,224 | 8/1984 | Enzmann et al. . |
| 4,503,569 | 3/1985 | Dotter . |
| 4,512,238 | 4/1985 | Balko et al. . |
| 4,516,972 | 5/1985 | Samson . |
| 4,531,933 | 7/1985 | Norton et al. . |
| 4,538,622 | 9/1985 | Samson et al. . |
| 4,547,194 | 10/1985 | Moorehead . |
| 4,553,545 | 11/1985 | Maass et al. . |
| 4,554,929 | 11/1985 | Samson et al. . |
| 4,560,374 | 12/1985 | Hammerslag . |
| 4,569,347 | 2/1986 | Frisbie . |
| 4,571,240 | 2/1986 | Samson et al. . |
| 4,572,186 | 2/1986 | Gould et al. . |
| 4,580,568 | 4/1986 | Gianturco . |
| 4,616,652 | 10/1986 | Simpson . |
| 4,619,246 | 10/1986 | Molgaard-Nielsen et al. . |
| 4,619,274 | 10/1986 | Morrison . |
| 4,649,922 | 3/1987 | Wiktor . |
| 4,650,466 | 3/1987 | Luther . |
| 4,655,771 | 4/1987 | Wallsten . |
| 4,665,918 | 5/1987 | Garza et al. . |
| 4,681,110 | 7/1987 | Garza et al. . |
| 4,706,671 | 11/1987 | Weinrib . |
| 4,732,152 | 3/1988 | Wallsten et al. . |
| 4,733,665 | 3/1988 | Palmaz . |
| 4,739,762 | 4/1988 | Palmaz . |
| 4,740,207 | 4/1988 | Kreamer . |
| 4,748,982 | 6/1988 | Horzewski et al. . |
| 4,748,986 | 6/1988 | Morrison et al. . |
| 4,760,849 | 8/1988 | Kropf . |
| 4,762,128 | 8/1988 | Rosenbluth . |
| 4,768,507 | 9/1988 | Fischell . |
| 4,771,777 | 9/1988 | Horzewski . |
| 4,775,371 | 10/1988 | Mueller, Jr. . |
| 4,776,337 | 10/1988 | Palmaz . |
| 4,787,899 | 11/1988 | Lazarus . |
| 4,790,315 | 12/1988 | Mueller, Jr. et al. . |
| 4,795,458 | 1/1989 | Regan . |
| 4,800,882 | 1/1989 | Gianturco . |
| 4,830,003 | 5/1989 | Wolff et al. . |
| 4,848,342 | 7/1989 | Kaltenbach . |
| 4,848,343 | 7/1989 | Wallsten et al. . |
| 4,856,516 | 8/1989 | Hillstead . |
| 4,870,966 | 10/1989 | Dellon et al. . |
| 4,877,030 | 10/1989 | Beck et al. . |
| 4,878,906 | 11/1989 | Lindemann et al. . |
| 4,886,062 | 12/1989 | Wiktor . |
| 4,892,539 | 1/1990 | Koch . |
| 4,893,623 | 1/1990 | Rosenbluth . |
| 4,907,336 | 3/1990 | Gianturco . |
| 4,913,141 | 4/1990 | Hillstead . |
| 4,921,479 | 5/1990 | Grayzel . |
| 4,922,905 | 5/1990 | Strecker . |
| 4,923,464 | 5/1990 | DiPisa, Jr. . |
| 4,950,227 | 8/1990 | Savin et al. . |
| 4,969,458 | 11/1990 | Wiktor . |
| 4,969,890 | 11/1990 | Sugita et al. . |
| 4,981,478 | 1/1991 | Evard et al. . |
| 4,986,831 | 1/1991 | King et al. . |
| 4,990,155 | 2/1991 | Wilkoff . |
| 4,994,071 | 2/1991 | MacGregor . |
| 4,998,539 | 3/1991 | Delsanti . |
| 5,002,560 | 3/1991 | Machold . |
| 5,007,926 | 4/1991 | Derbyshire . |
| 5,015,253 | 5/1991 | MacGregor . |
| 5,019,085 | 5/1991 | Hillstead . |
| 5,019,090 | 5/1991 | Pinchuk . |
| 5,026,377 | 6/1991 | Burton et al. . |
| 5,034,001 | 7/1991 | Garrison et al. . |
| 5,035,706 | 7/1991 | Giantureo et al. . |
| 5,037,377 | 8/1991 | Alonso . |
| 5,037,392 | 8/1991 | Hillstead . |
| 5,037,427 | 8/1991 | Harada et al. . |
| 5,041,126 | 8/1991 | Gianturco . |
| 5,059,211 | 10/1991 | Stack et al. . |
| 5,061,273 | 10/1991 | Yock . |
| 5,061,275 | 10/1991 | Wallsten et al. . |
| 5,062,829 | 11/1991 | Pryor et al. . |
| 5,064,435 | 11/1991 | Porter . |
| 5,071,407 | 12/1991 | Termin et al. . |
| 5,078,720 | 1/1992 | Burton et al. . |
| 5,078,726 | 1/1992 | Kreamer . |
| 5,078,736 | 1/1992 | Behl . |
| 5,084,065 | 1/1992 | Weldon et al. . |
| 5,089,005 | 2/1992 | Harada . |
| 5,089,006 | 2/1992 | Stiles . |
| 5,092,877 | 3/1992 | Pinchuk . |
| 5,100,429 | 3/1992 | Sinofsky et al. . |
| 5,102,417 | 4/1992 | Palmaz . |
| 5,104,404 | 4/1992 | Wolff . |
| 5,108,416 | 4/1992 | Ryan et al. . |
| 5,108,417 | 4/1992 | Sawyer . |
| 5,116,318 | 5/1992 | Hollstead . |
| 5,116,360 | 5/1992 | Pinchuk et al. . |
| 5,116,365 | 5/1992 | Hillstead . |
| 5,122,154 | 6/1992 | Rhodes . |
| 5,123,917 | 6/1992 | Lee . |
| 5,133,732 | 7/1992 | Wiktor . |
| 5,135,503 | 8/1992 | Abrams . |
| 5,135,517 | 8/1992 | McCoy . |
| 5,135,536 | 8/1992 | Hillstead . |
| 5,158,548 | 10/1992 | Lau et al. . |
| 5,161,547 | 11/1992 | Tower . |
| 5,163,903 | 11/1992 | Crittenden et al. . |
| 5,163,951 | 11/1992 | Pinchuk et al. . |
| 5,163,952 | 11/1992 | Froix . |
| 5,163,958 | 11/1992 | Pinchuk . |
| 5,171,262 | 12/1992 | MacGregor . |
| 5,176,661 | 1/1993 | Evard et al. . |
| 5,180,367 | 1/1993 | Kontos et al. ............ 604/101 |
| 5,183,085 | 2/1993 | Timmermans . |
| 5,192,297 | 3/1993 | Hull . |
| 5,192,307 | 3/1993 | Wall . |
| 5,192,311 | 3/1993 | King et al. . |
| 5,195,984 | 3/1993 | Schatz . |
| 5,197,978 | 3/1993 | Hess . |
| 5,234,416 | 8/1993 | Macaulay et al. . |
| 5,242,399 | 9/1993 | Lau . |
| 5,290,230 | 3/1994 | Ainsworth et al. . |
| 5,290,295 | 3/1994 | Querals et al. . |
| 5,300,025 | 4/1994 | Wantink . |
| 5,415,664 | 5/1995 | Pinchuk . |
| 5,445,646 | 8/1995 | Euteneuer et al. . |
| 5,453,090 | 9/1995 | Martinez et al. . |
| 5,522,882 | 6/1996 | Gaterud et al. . |
| 5,534,007 | 7/1996 | St. Germain et al. . |
| 5,554,118 | 9/1996 | Jang ..................... 604/102 |
| 5,571,135 | 11/1996 | Fraser et al. . |
| 5,628,755 | 5/1997 | Heller et al. . |
| 5,776,141 | 7/1998 | Klein et al. .............. 606/198 |
| 5,817,100 | 10/1998 | Igaki ..................... 623/1 |
| B1 4,323,071 | 5/1980 | Simpson et al. . |

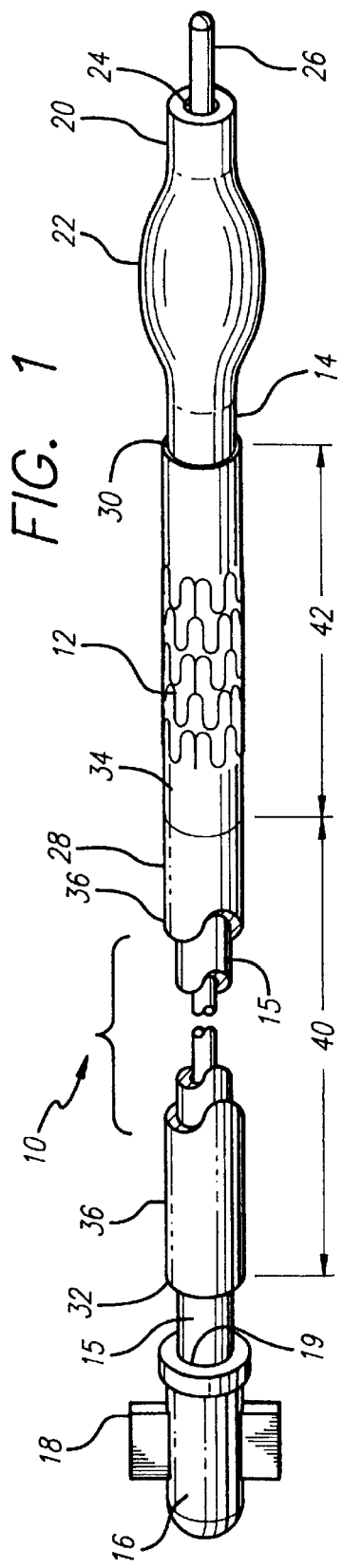
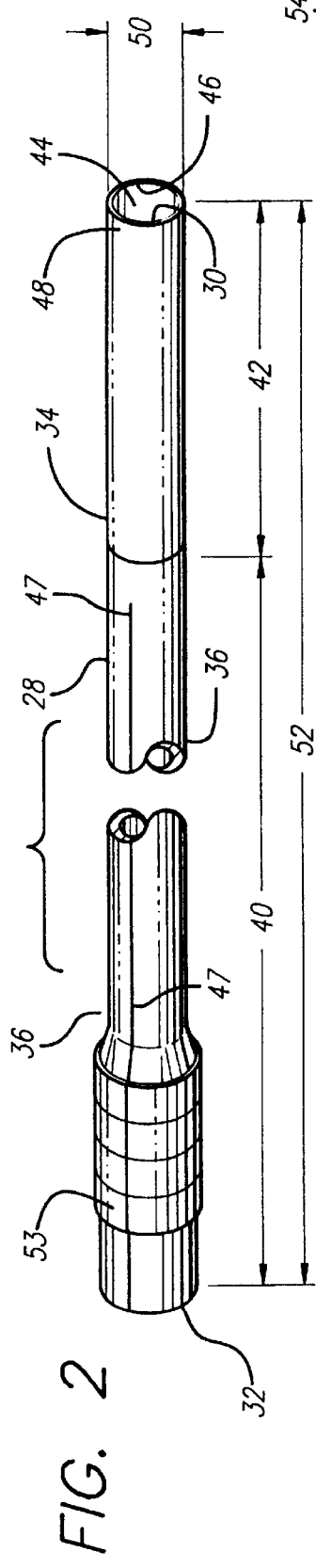
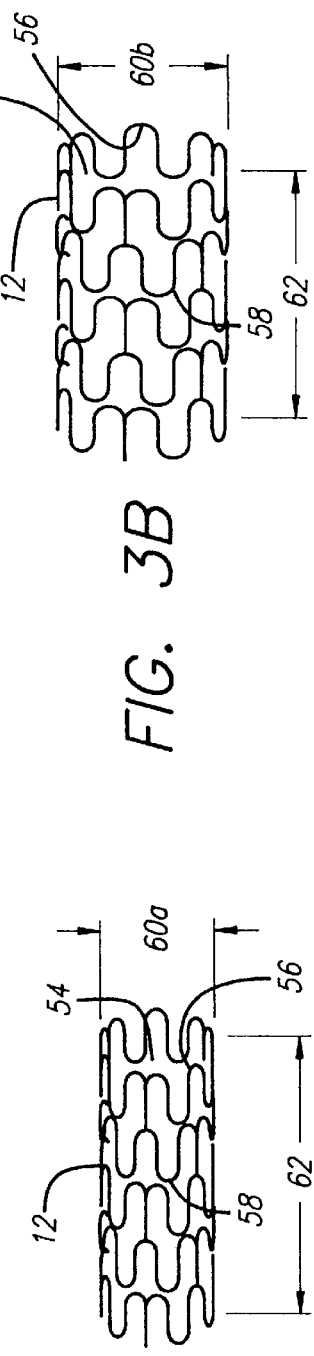

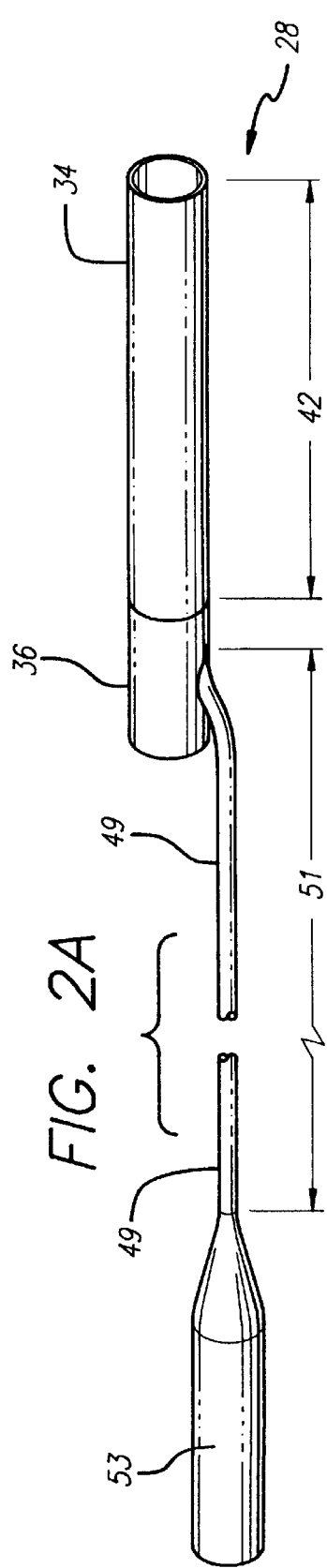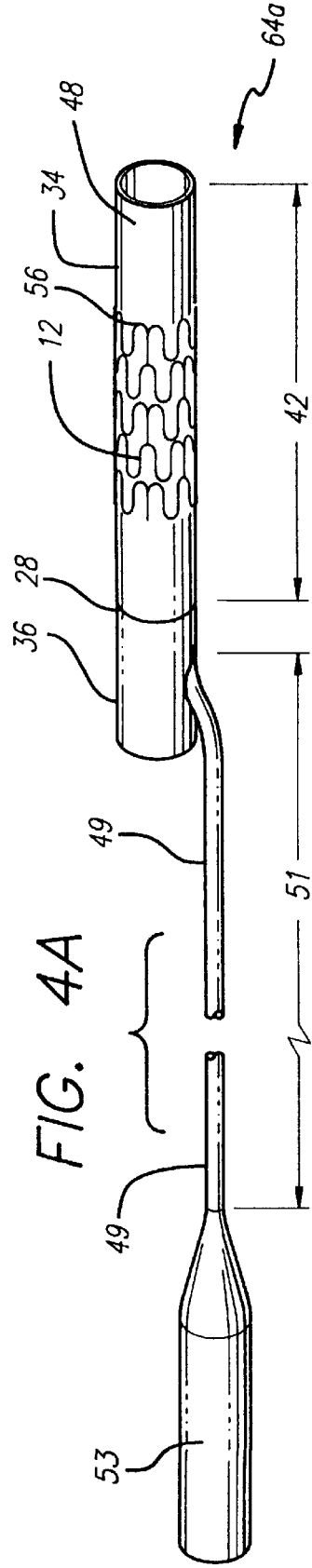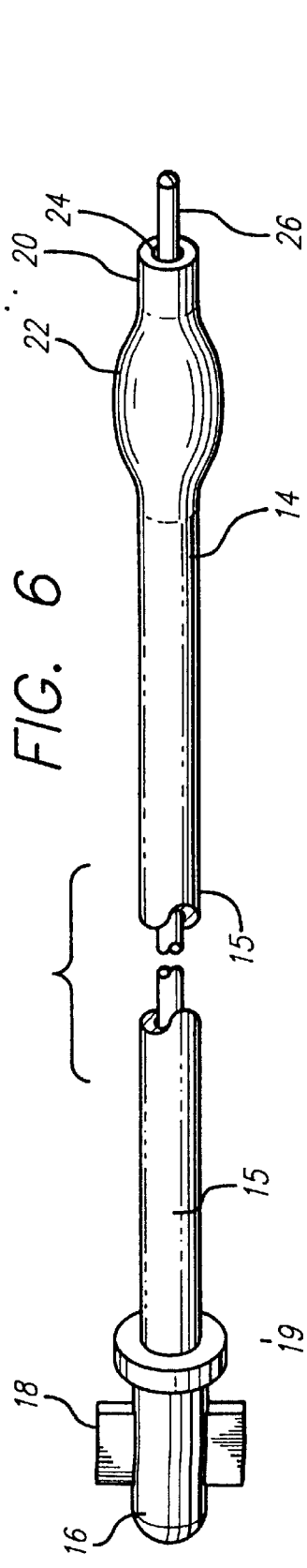
FIG. 2A
FIG. 4A
FIG. 6

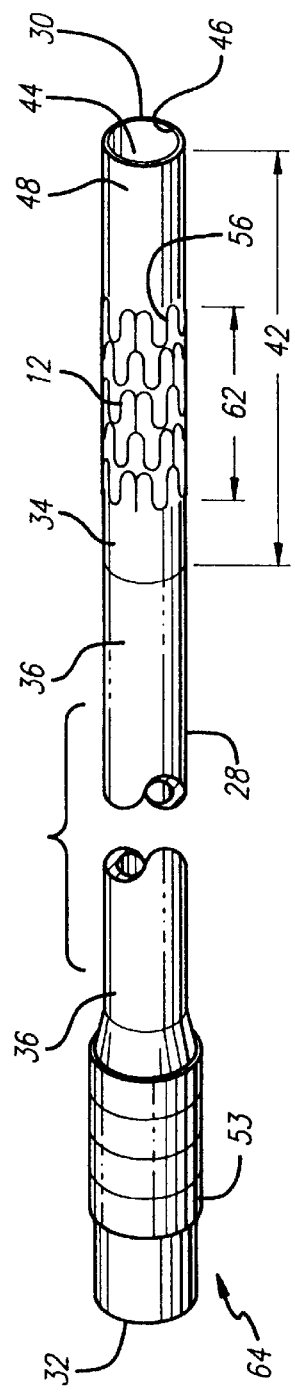
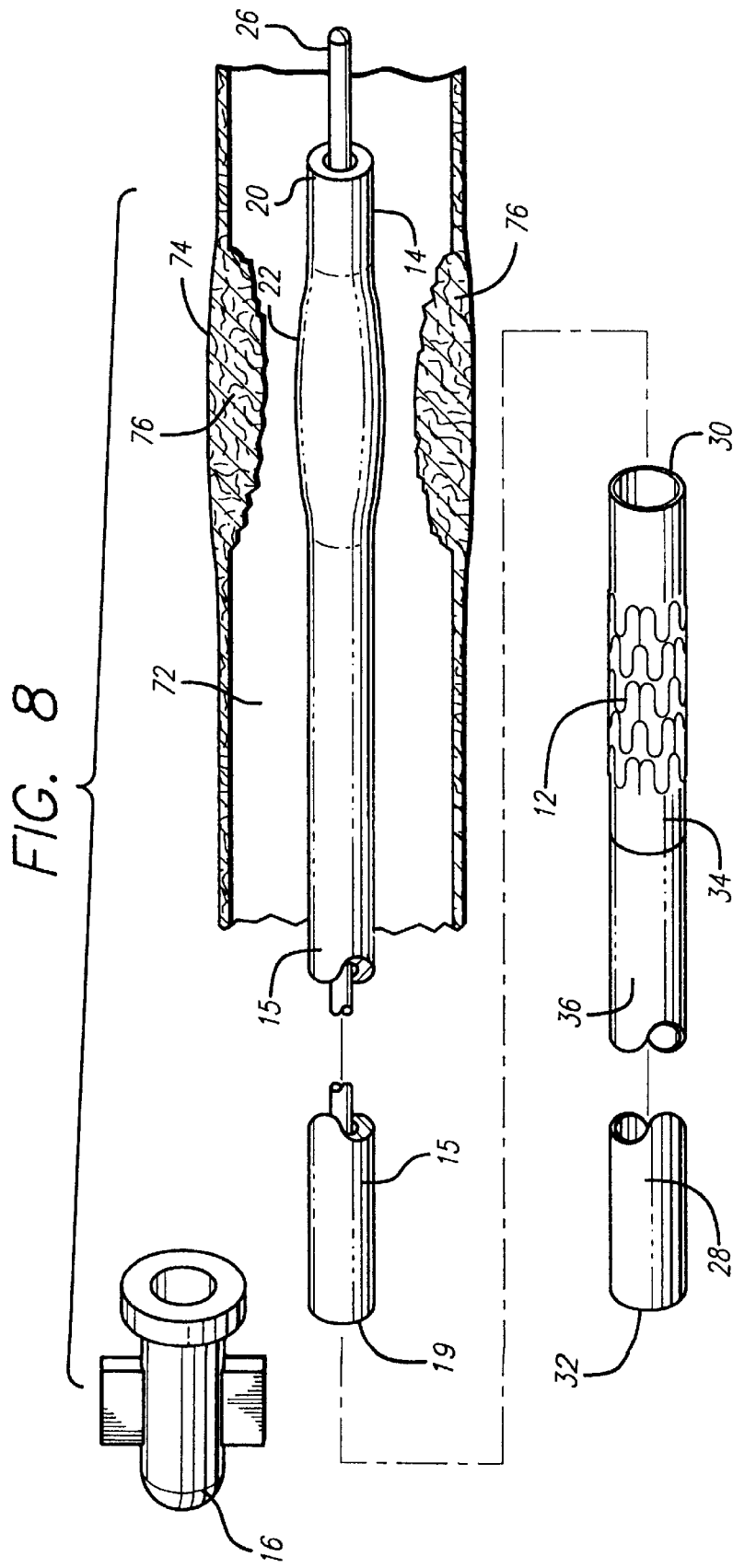

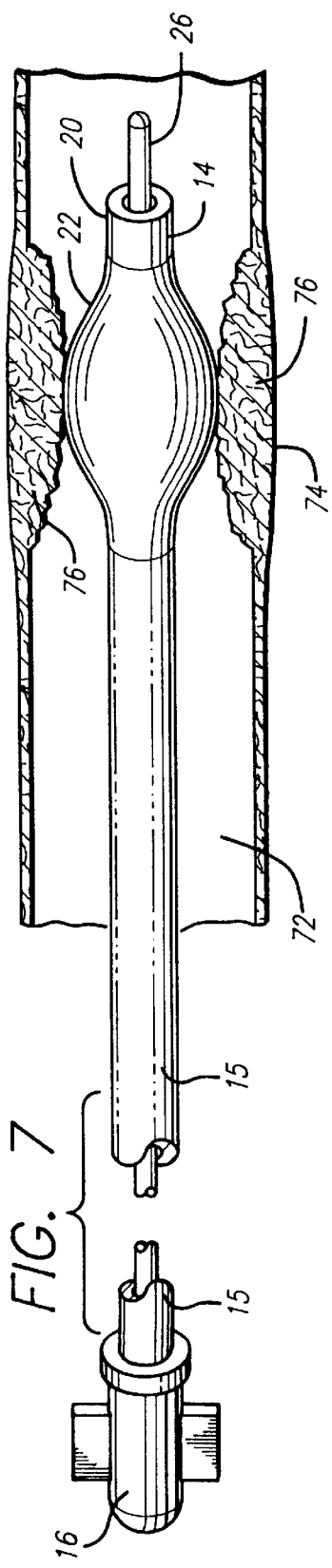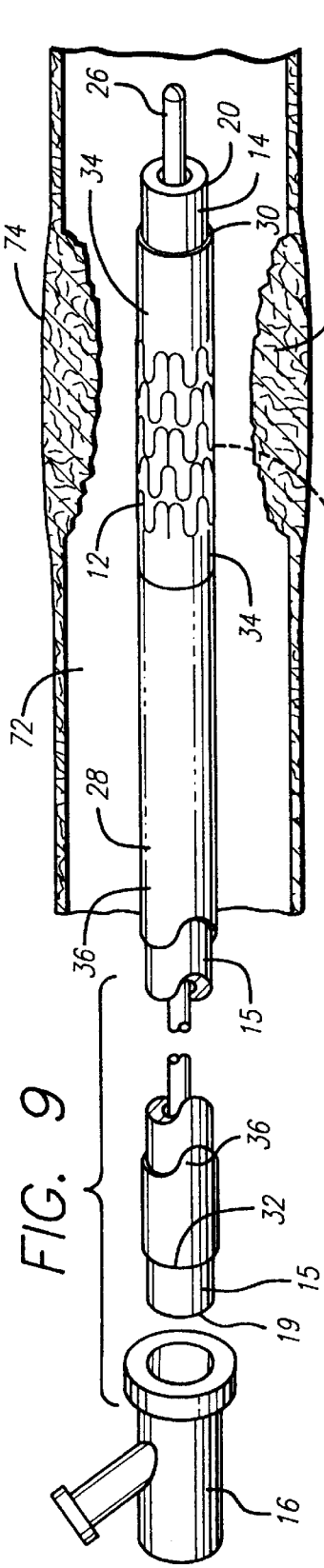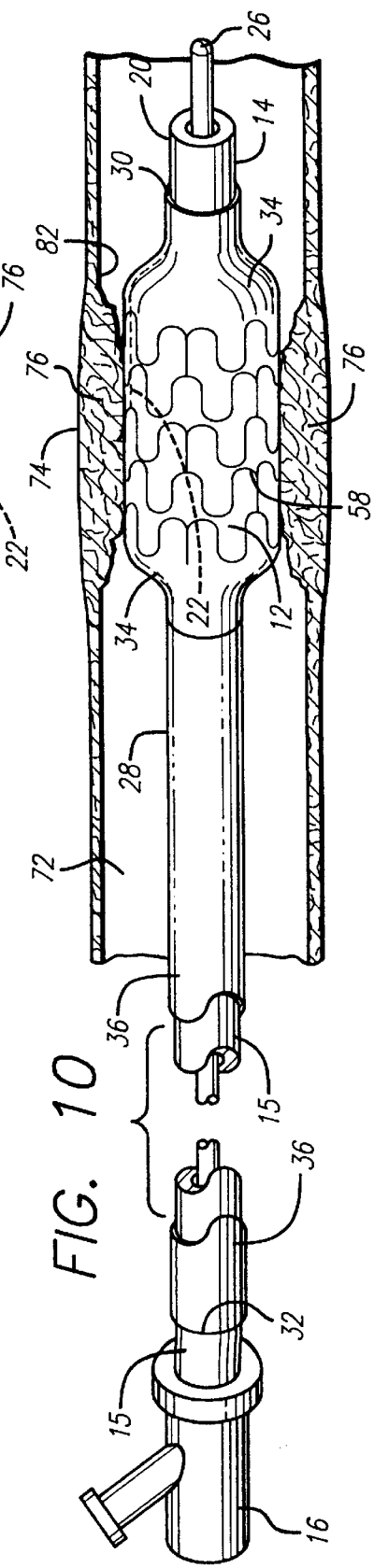

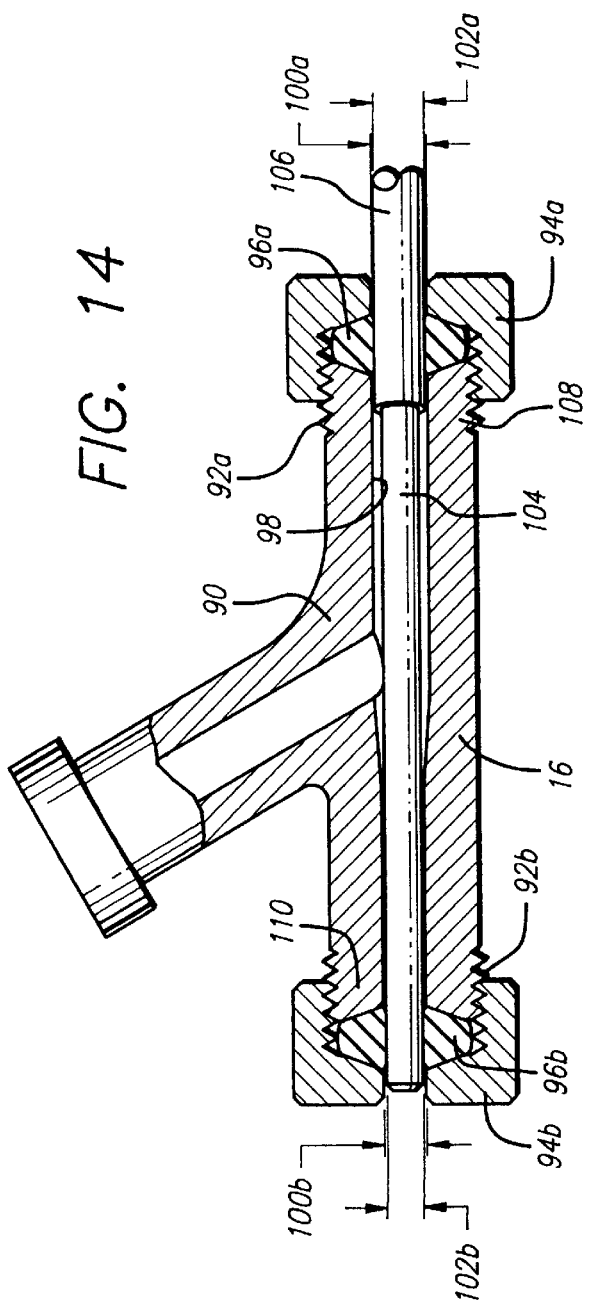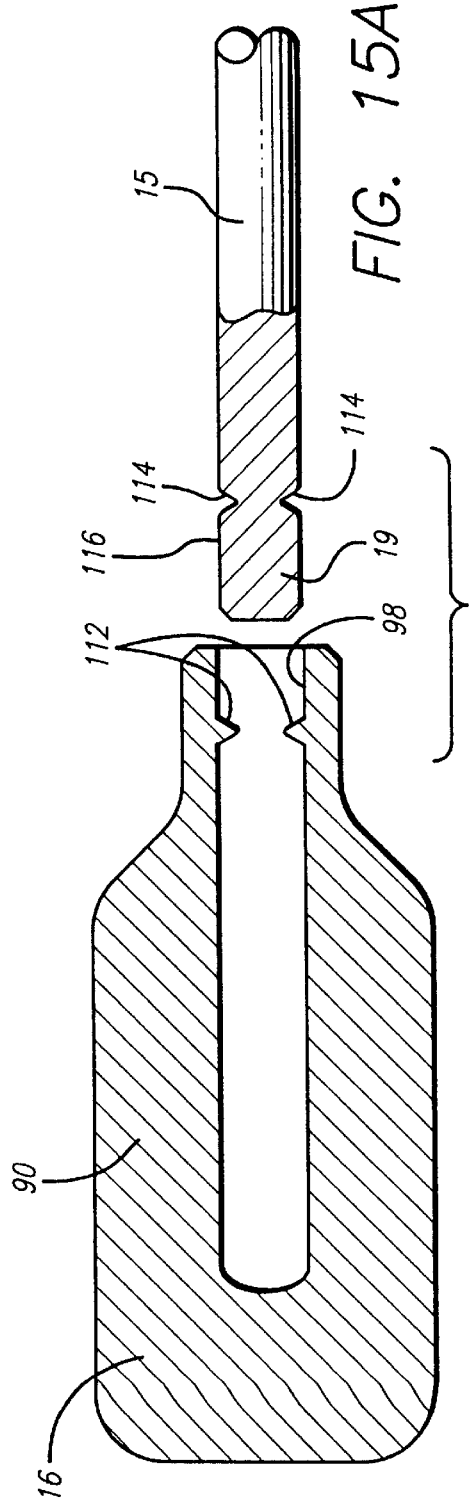
FIG. 14
FIG. 15A

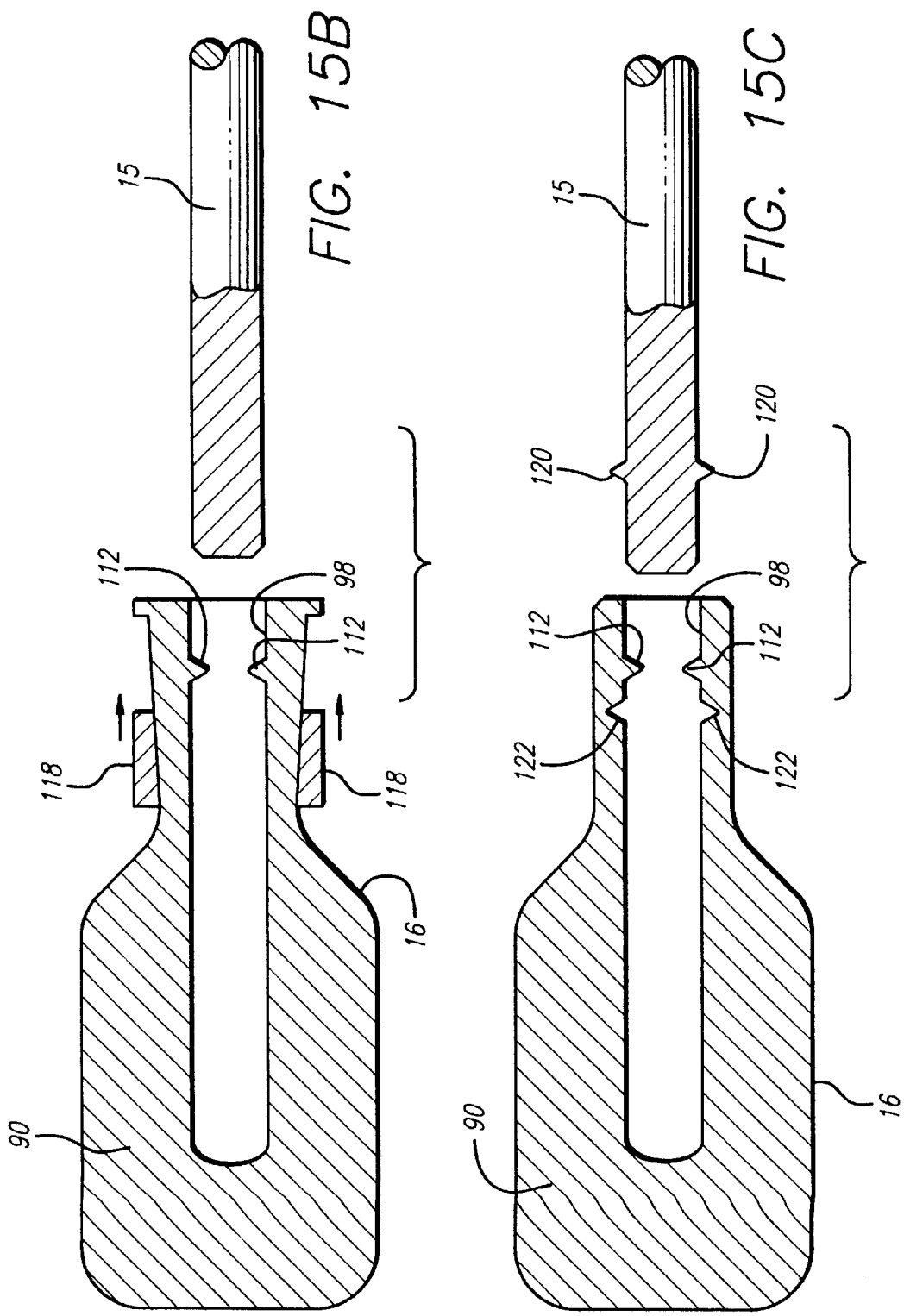

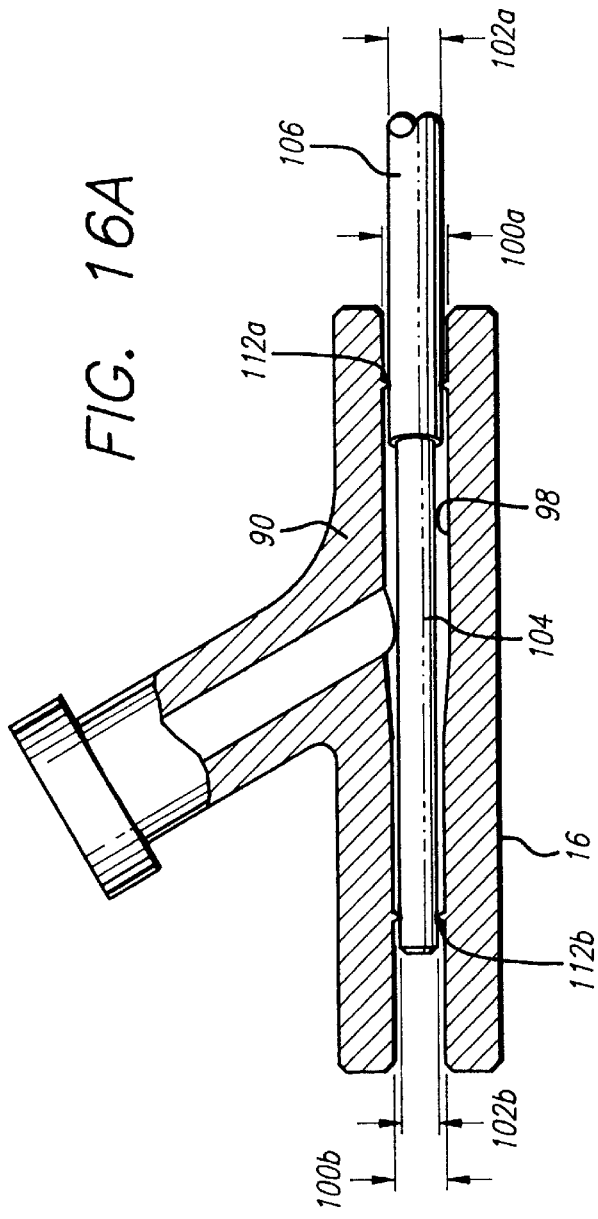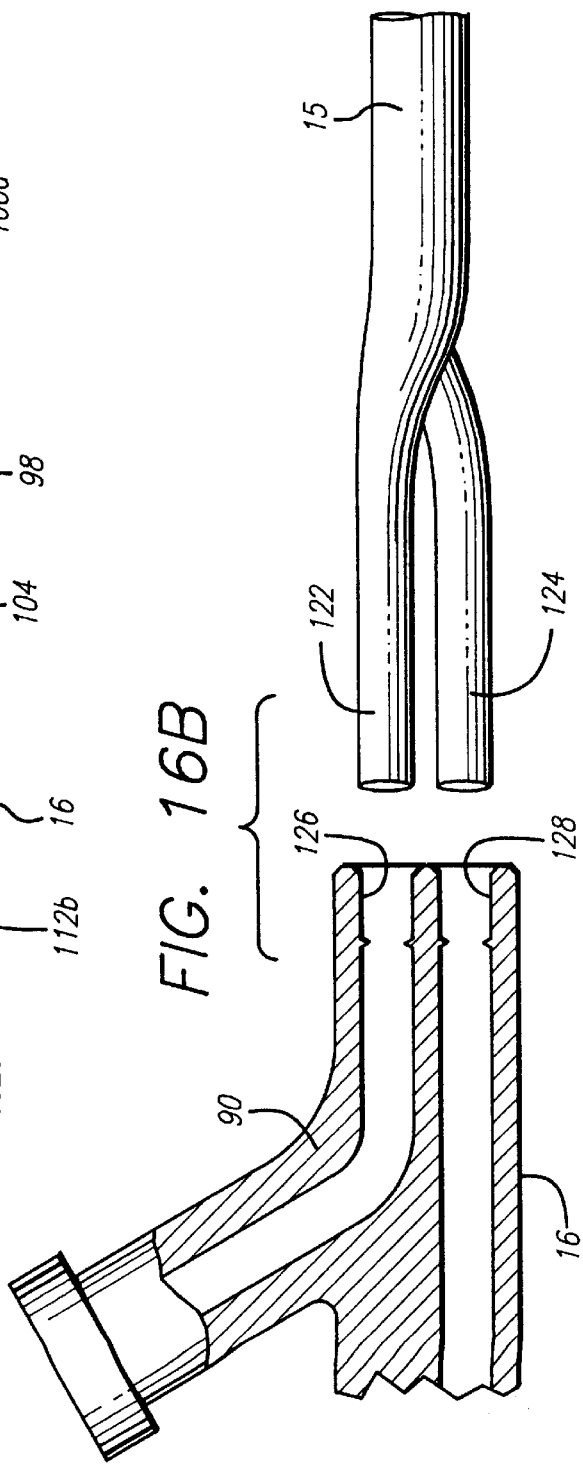

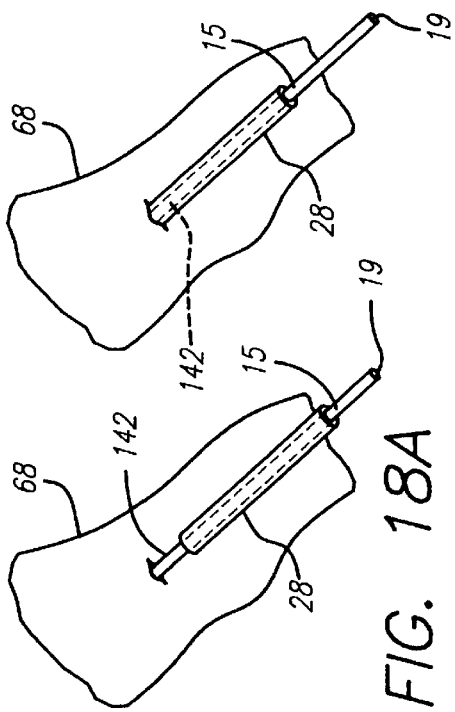
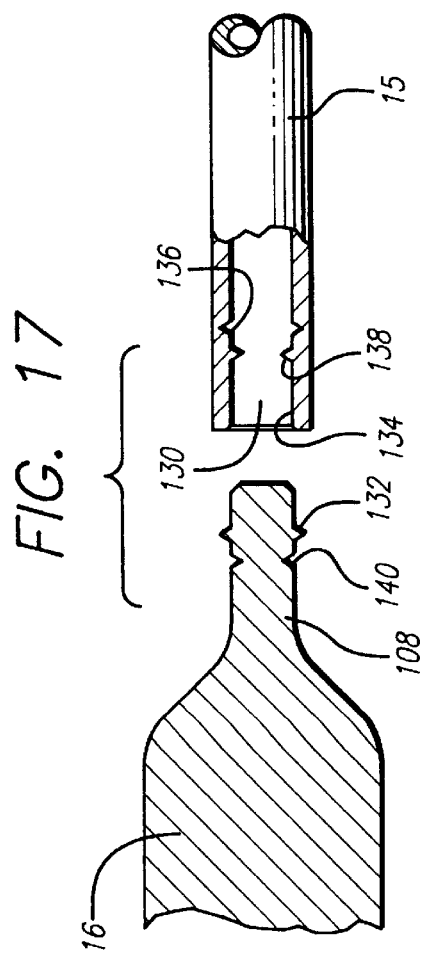
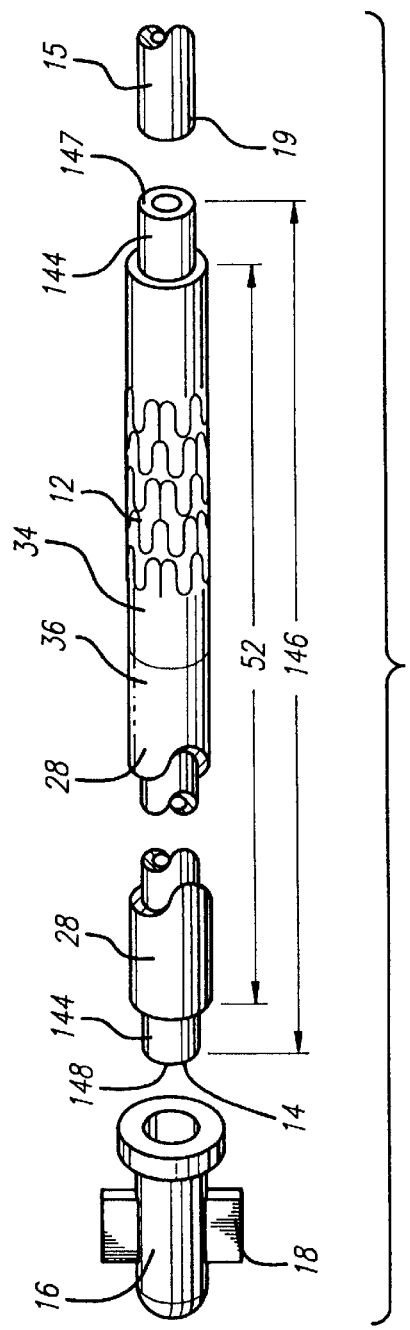

CATHETER AND METHOD FOR A STENT DELIVERY SYSTEM

BACKGROUND OF THE INVENTION

1. Field of the Invention

The invention relates to stent delivery systems, which are used to implant a stent into a patient's body lumen to maintain the patency thereof. More particularly, the present invention relates to a catheter having a removable proximal hub to allow a stent delivery sheath to be loaded and unloaded from the catheter without necessitating the withdrawal of the catheter from the patient.

2. Description of Related Art

Stents are generally cylindrically-shaped devices which function to hold open and sometimes expand a segment of a blood vessel or other body lumen. They are particularly suitable for use to support and hold back a dissected arterial lining which can occlude the fluid passageway. Stents also are useful in maintaining the patency of a body lumen, such as a coronary artery, after a percutaneous transluminal coronary angioplasty (PTCA) procedure or an atherectomy procedure to open a stenosed area of the artery. Several interventional treatment modalities are presently used for heart disease, including balloon and laser angioplasty, atherectomy, and bypass surgery.

In typical balloon angioplasty procedures, a guiding catheter having a preformed distal tip is percutaneously introduced through the femoral artery into the cardiovascular system of a patient in a conventional Seldinger technique and advanced within the cardiovascular system until the distal tip of the guiding catheter is seated in the ostium of a desired coronary artery. A guidewire is positioned within an inner lumen of a dilatation catheter, and then both are advanced through the guiding catheter to the distal end thereof. The guidewire is advanced out of the distal end of the guiding catheter into the patient's coronary vasculature until the distal end of the guidewire crosses a lesion to be dilated. Next, the dilatation catheter, having an inflatable balloon on the distal portion thereof, is advanced into the patient's coronary anatomy over the previously-introduced guidewire until the balloon of the dilation catheter is properly positioned across the lesion. Once in position across the lesion, the balloon, which is typically made of relatively inelastic materials, is inflated to a predetermined size with liquid at relatively high pressure (e.g., greater than 4 atmospheres) to compress the arteriosclerotic plaque of the lesion against the inside of the artery wall and to otherwise expand the inner lumen of the artery. The dilatation balloon is then deflated so that blood flow can be resumed through the dilated artery and the dilation catheter can be removed. Further details of dilation catheters, guidewires, and devices associated therewith for angioplasty procedures can be found in U.S. Pat. No. 4,323,071 (Simpson-Robert); U.S. Pat. No. 4,439,185 (Lindquist); U.S. Pat. No. 4,516,972 (Samson); U.S. Pat. No. 4,538,622 (Samson, et al.); U.S. Pat. No. 4,554,929 (Samson, et al.); U.S. Pat. No. 4,616,652 (Simpson); U.S. Pat. No. 4,638,805 (Powell); and U.S. Pat. No. 4,748,982 (Horzewski, et al.) which are incorporated herein in their entirety by reference thereto.

A major problem that can occur during balloon angioplasty procedures is the formation of intimal flaps that can collapse and occlude the artery when the balloon is deflated at the end of the angioplasty procedure. Another major problem characteristic of balloon angioplasty procedures is the large number of patients which are subject to restenosis in the treated artery. In the case of restenosis, the treated artery may again be subject to balloon angioplasty or to other treatments such as bypass surgery, if additional balloon angioplasty procedures are not warranted. However, in the event of a partial or total occlusion of an artery resulting from the collapse of a dissected arterial lining after the dilation balloon is deflated, the patient may require immediate medical attention, particularly where the occlusion occurs in a coronary artery.

A major focus of recent development work in the treatment of heart disease has been directed to endoprosthetic devices called stents. Stents are generally cylindrically-shaped intravascular devices that are placed within a damaged artery to hold it open. Such devices can be used to prevent restenosis or to tack up an intimal flap to maintain the patency of the blood vessel immediately after intravascular treatments such as PTCA.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

However, the rapid and effective delivery of a stent to the desired location within a patient's vasculature is difficult and time consuming, particularly where stent deployment is accompanied by a balloon angioplasty procedure or where multiple stents are deployed in the body lumen.

It may therefore be important to improve existing stent delivery systems to provide rapid stent delivery while at the same time allowing a cardiologist to select a desired stent and catheter combination. The present invention satisfies these needs.

SUMMARY OF THE INVENTION

The present invention is directed to an apparatus and method for deploying one or more stents within a body lumen, without necessitating removal of the catheter from the body lumen prior to stent deployment. The invention generally comprises a stent deployment catheter having a shaft with a detachable proximal hub removably secured to a proximal end of the shaft.

In a preferred embodiment, the catheter shaft has an expandable member at the shaft distal end. The detachable proximal hub may include a control device for controlling expansion of the expandable member. The catheter may also include a securing device that prevents rotation of the detachable proximal hub about the shaft axis when the proximal hub is secured to the shaft. Such a securing device may include one or more projections extending from the detachable proximal hub that are configured to be received in one or more apertures in the catheter shaft.

The stent deployment catheter may, in a preferred embodiment, comprise a part of a stent deployment system. Such a stent deployment system generally comprises the aforementioned catheter with a shaft and detachable proximal hub; a substantially tubular sheath configured to slidably move over the catheter shaft; and a substantially tubular stent positioned over a distal portion of the sheath.

The substantially tubular sheath preferably has proximal and distal ends, proximal and distal portions, an outer surface, and a lumen therethrough defining an inner surface. The sheath is configured for slidable movement over the catheter shaft. The distal portion of the sheath comprises a flexible, expandable material extending from the inner surface of the sheath to the outer surface of the sheath. The proximal portion of the sheath is resistant to compressive forces.

The catheter preferably includes an expandable device, such as a dilatation device or a balloon, at its distal end. The substantially tubular stent is preferably a radially expandable stent having a delivery configuration and a deployed configuration. The stent is positioned in the delivery configuration over the distal portion of the sheath.

In a preferred embodiment, the catheter is a dilatation catheter with an expandable member at the catheter shaft distal end. The catheter may be introduced into the body lumen such that the expandable member is at a desired treatment site, and the expandable member then expanded to dilate the body lumen.

In one preferred method of operation, once the body lumen has been dilated by the dilatation device, the removable proximal hub can removed, and the sheath can be longitudinally slid onto and over the sheath until the sheath distal portion bearing the stent is positioned over the expandable member. The expandable member can then be expanded. Because the sheath distal portion is formed of an elastomeric material, the sheath distal portion expands as the dilatation device expands. This expansion of the dilatation device and sheath distal portion also expands and deploys the stent at the desired location. The dilatation device can then be deflated, thereby causing the sheath distal portion to resume its unexpanded form. The stent retains its deployed, expanded form, and remains in the body lumen.

In another preferred method of operation, the removable proximal hub is removed, and the sheath longitudinally slid onto and over the sheath, prior to dilatation of the body lumen. The sheath distal portion bearing the stent is positioned just proximal of the expandable member. Because the stent is proximal of the expandable member, expansion of the expandable member to dilate the body lumen will not cause the stent to deploy. After dilatation is performed, the sheath is advanced so that the sheath distal portion bearing the stent is positioned over the expandable member. The expandable member is expanded, thereby expanding and deploying the stent at the treatment site.

In another embodiment, body lumen dilatation and stent deployment occur as a single step. In such an embodiment, the removable proximal hub is removed, and the sheath longitudinally slid onto and over the sheath until the sheath distal portion bearing the stent is positioned over the expandable member. The expandable member is then expanded, thereby causing the stent to expand and assume its deployed configuration. Expansion of the stent and expandable member also dilate the body lumen, so that stent deployment and dilatation of the body lumen occur as a single step.

After the stent is deployed, the proximal hub can again be removed to allow the sheath to be slidably removed from the catheter shaft. A new sheath, bearing one or more additional stents, can then be slid onto the catheter shaft and thereby introduced into the body lumen at a selected site. The proximal hub can then be reattached, and the new stent or stents deployed at desired locations. These steps can be repeated for several additional sheaths and stents, without requiring the catheter to be withdrawn from the body lumen until deployment of all stents is completed.

The invention is applicable to various catheter designs, including so-called over-the-wire (OTW) as well as rapid-exchange catheters. Examples of rapid-exchange catheters are shown and described in U.S. Pat. No. 5,180,368 (Garrison), U.S. Pat. No. 5,458,613 (Gharibadeh et al.), and U.S. Pat. No. 5,496,346 (Horzewski et al.).

Other features and advantages of the present invention will become more apparent from the following detailed description of the invention when taken in conjunction with the accompanying drawings.

BRIEF DESCRIPTION OF THE DRAWINGS

FIG. 1 is a perspective view, partially in section, depicting a delivery catheter, sheath, and stent assembly according to the present invention.

FIG. 2 is a perspective view of a sheath according to the present invention.

FIG. 2a is a perspective view of an alternative embodiment of a sheath according to the present invention.

FIG. 3a is a perspective view of a stent in a delivery configuration.

FIG. 3b is a perspective view of the stent of FIG. 3a in a deployed configuration.

FIG. 4 is a perspective view of a sheath and stent assembly according to the present invention.

FIG. 4a is a perspective view of a sheath and stent assembly according to an alternative embodiment of the present invention.

FIG. 6 is a perspective view of a delivery catheter according to the invention.

FIG. 7 is a perspective view of the delivery catheter with the dilatation balloon expanded to dilate a body lumen.

FIG. 8 is a perspective view of the catheter of FIG. 7, with sheath and stent assembly, and with the proximal hub detached from the catheter according to a preferred embodiment of the current invention.

FIG. 9 is a perspective view depicting the delivery catheter of FIG. 6 with a sheath and stent assembly, with the stent positioned for deployment in the body lumen.

FIG. 10 is a perspective view depicting the delivery catheter, sheath, and stent assembly of FIG. 9 with the balloon expanded to deploy the stent in the body lumen.

FIG. 13b is a cross-sectional view of a proximal portion of the delivery catheter of FIG. 13a.

FIG. 14 is a cross-sectional view of a proximal portion of a delivery catheter according to an embodiment of the invention.

FIG. 15a is a cross-sectional view of a proximal portion of a delivery catheter according to the invention.

FIG. 15b is a cross-sectional view of a proximal portion of a delivery catheter according to a further embodiment of the invention.

FIG. 15c is a cross-sectional view of a proximal portion of a delivery catheter according to a further embodiment of the invention.

FIG. 16a is a cross-sectional view of a proximal portion of a coaxial delivery catheter according to the invention.

FIG. 16b is a cross-sectional view of a proximal portion of a dial-lumen delivery catheter according to a further embodiment of the invention.

FIG. 17 is a cross-sectional view of a proximal portion of a delivery catheter according to the invention.

FIG. 18a is a perspective view of a proximal portion of a delivery catheter and sheath used to deploy a stent in a patient.

FIG. 18b is a perspective view of the delivery catheter and sheath of FIG. 18a.

FIG. 19 is a perspective view of a delivery catheter having an extender section according to the invention.

DETAILED DESCRIPTION OF THE PREFERRED EMBODIMENTS

Figure 5:
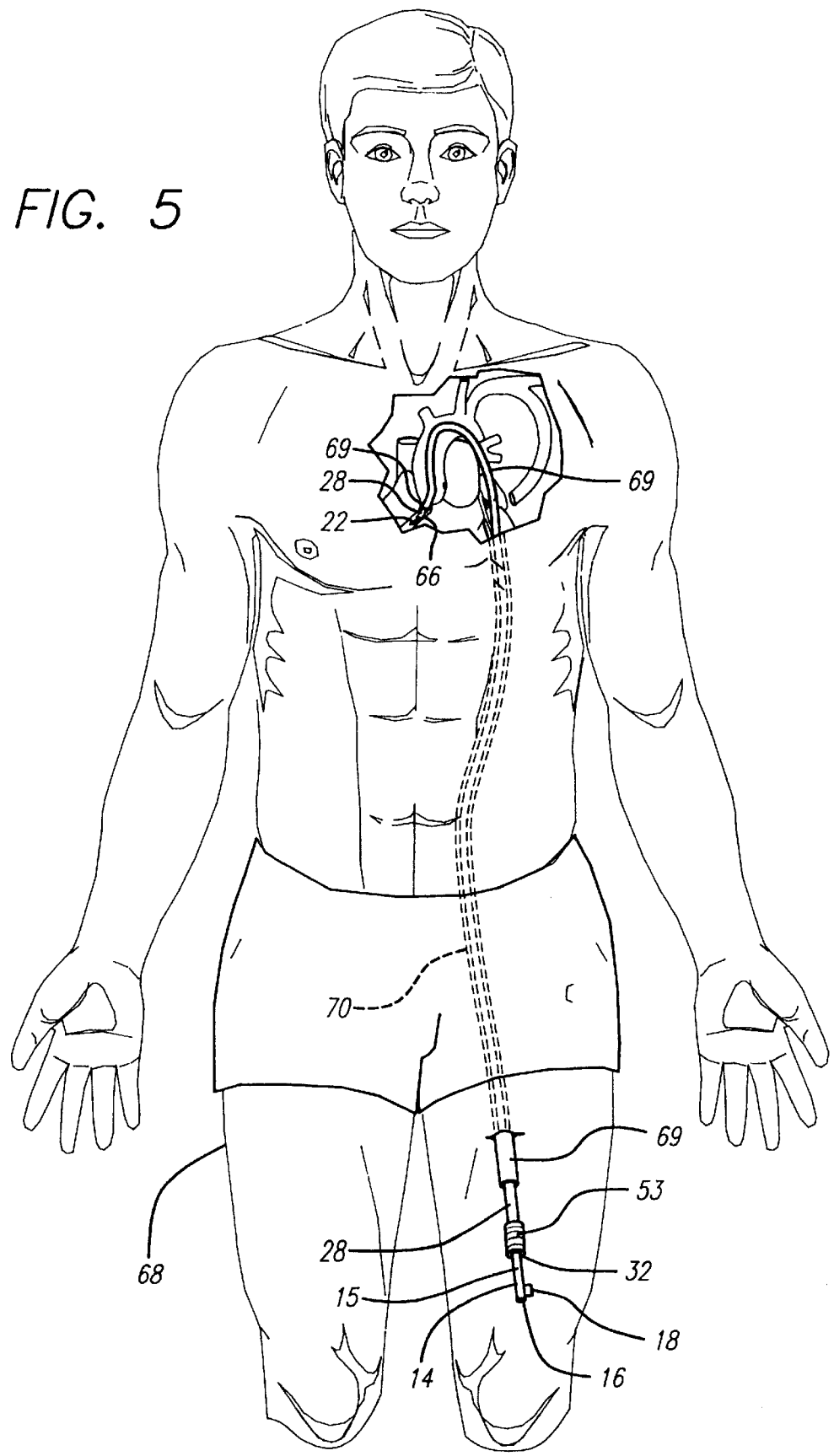
FIG. 5 is a perspective view, partially in section, of a delivery catheter and sheath assembly used to deploy a stent in a human patient according to the present invention.

The present invention is depicted in FIGS. 1–19 for use in various body lumens and procedures, including use in deploying stents in dilated arteries during balloon angioplasties. However, the present invention is not limited to use in blood vessels or angioplasties, but can be used in other body lumens and procedures to deploy stents, endovascular grafts, and similar devices.

Referring to FIG. 1, in one preferred embodiment the assembly 10 for deploying a stent 12 comprises a balloon catheter 14. The balloon catheter 14 comprises a removable proximal hub 16 having various controls 18 located thereon, which is secured to a proximal end 19 of a catheter shaft 15. The catheter shaft 15 has a distal end 20 having a dilatation device, which in the embodiment shown is a dilatation balloon 22. In the embodiment shown, the balloon catheter shaft 15 has an inner lumen 24 that allows a guidewire 26 to pass therethrough.

The assembly 10 further comprises a sheath 28 having a distal end 30 and a proximal end 32. The sheath 28, which is shown in greater detail in FIG. 2, comprises two portions—a distal portion 34 and a proximal portion 36. The distal portion 34 preferably comprises an elastic, expandable material that can be expanded by outward pressure from within the sheath 28. The proximal portion 36 is preferably formed of a material that enhances the pushability of sheath 28 yet is flexible enough to navigate the vascular system. The proximal portion length 40 is typically several times the distal portion length 42.

The sheath 28 shown in FIG. 2 has an inner lumen 44 passing along the length of the sheath 28. The sheath has an inner surface 46, defined by the inner lumen 44, and an outer surface 48. The inner lumen 44 is sized for slidable movement over the dilatation balloon catheter shaft 15.

The sheath 28 of FIG. 2 has an outer diameter 50 sized to pass within a body lumen. The sheath 28 preferably has a length 52 that allows the sheath distal end 30 to be positioned at a desired treatment site in a body lumen while the sheath proximal end 32 is positioned outside of the body lumen and patient, so that a user can manipulate the sheath 28 by grasping and maneuvering the sheath proximal end 32. The precise sheath length 52 will be determined by the particular application.

The sheath 28 may include a slit 47 extending from the sheath proximal end 32 toward the sheath distal end 30. The slit 47 allows the sheath to be peeled apart to facilitate introduction or removal of various devices, such as a catheter or guidewire, via the side of the sheath.

FIG. 2a shows an alternative embodiment of a delivery sheath 28 having a distal portion 34 configured to receive a stent, but wherein most of the proximal portion is replaced by a mandrel 49. The mandrel 49 performs much as the proximal portion 36 described above with respect to FIG. 2. The mandrel 49 is preferably formed of a material such as a polymer, stainless steel, titanium, nickel-titanium alloy, fiber reinforced polymers, braided polymers, and braid reinforced polymers that enhance the pushability of the sheath 28 yet is flexible enough to navigate the vascular system. The mandrel length 51 is typically several times the length 42 of the distal portion 34. While the sheath proximal portion 36 shown in FIG. 2 was configured to slidably pass over a catheter, the mandrel 49 of FIG. 11 is configured to pass and lie alongside a catheter. The mandrel 49 may include a handle 53 by which a user can grasp the device. Such an embodiment may be used with so-called rapid exchange catheters, and particularly with a rapid-exchange catheter having a removable proximal hub according to the current invention.

FIGS. 3a and 3b show an expandable stent 12 for use with the balloon catheter 14 and sheath 28 of the current invention. The stent has an inner lumen 54 defining an inner surface 56, and an outer surface 58 defining an outer diameter 60a. FIG. 3a shows the stent 12 in its delivery configuration, whereby the outer diameter 60a is small enough to pass within a body lumen. FIG. 3b shows the stent 12 in its deployed configuration, whereby the outer diameter 60b is sized so that the stent outer surface 58 contacts the walls of the body lumen. The length 62 of the stent 12 is typically in the range of 5 to 50 mm, and preferably about 10 to 20 mm, but stents of almost any length may be used with the invention, depending on the particular application. FIGS. 3a and 3b show a stent 12 of an open lattice configuration, similar to the stent described in co-pending and commonly owned U.S. Ser. No. 08/454,599, which is incorporated herein by reference. However, other stent types and configurations are well known in the art and also are compatible with the invention, so long as the stent defines an inner lumen and can be partially or fully expanded with a dilatation device such as a balloon catheter.

FIG. 4 shows a stent and sheath assembly 64 for use with the current invention, with the sheath 28 similar to that previously described with respect to FIG. 2. The stent 12 is positioned in its delivery configuration on the sheath distal portion 34, with the stent inner surface 56 contacting the sheath outer surface 48. In the embodiment shown, the sheath distal portion length 42 is greater than the stent length 62, so that the stent 12 can be mounted entirely on the sheath distal portion 34 without contacting the sheath proximal portion 36. FIG. 4a shows an alternative embodiment of a stent and sheath assembly 64a, wherein the sheath 28 comprises a distal portion 34 and a mandrel 49, as was previously shown and described with respect to FIG. 2a.

The sheath and stent assembly are described in greater detail in concurrently-filed U.S. Ser. No. 08/840,487, entitled SHEATH AND METHOD FOR A STENT DELIVERY SYSTEM, with Jefferey Bleam and Andrew Mackenzie as inventors, which is incorporated herein by reference.

FIG. 5 shows the catheter, sheath, and stent assembly used in a balloon angioplasty procedure to deploy a stent 12 in a coronary artery 66 in a patient 68. The assembly has been percutaneously introduced through the femoral artery 70 into the cardiovascular system of the patient 68, with the dilatation balloon 22 positioned at a desired location to be treated. Both the catheter proximal hub 16, which includes the catheter controls 18, and the sheath proximal end 32 are positioned outside of the patient 68 so that a user may easily grasp and manipulate the catheter 14 and sheath 28. The user may also remove the catheter proximal hub 16 from the catheter shaft proximal end 19 without having to remove the catheter shaft 15 from the patient 68.

FIG. 6 shows a catheter according to the current invention. The balloon catheter 14 includes a removable proximal hub 16 having various controls 18 located thereon. The proximal hub 16 can be removably secured to a proximal end 19 of a catheter shaft 15. In a preferred embodiment, the catheter shaft 15 has a distal end 20 having a dilatation device, which in the embodiment shown is a dilatation balloon 22. In the embodiment shown in FIG. 6, the balloon catheter shaft 15 has an inner lumen 24 that allows a guidewire 26 to pass therethrough.

Referring now to FIG. 7, the catheter is shown with the dilatation balloon 22 positioned within a body lumen 72 at a desired treatment location 74, and the detachable proximal hub 16 positioned outside the patient's body. The desired treatment location 74 may comprise blockage 76, such as a stenosis caused by deposits of plaque, that partially occludes the body lumen 72. With the dilatation balloon 22 positioned at the desired treatment location 74, the dilatation balloon 22 is expanded, thereby dilating the blockage 76 and body lumen 72. With dilatation completed, the dilatation balloon 22 can be deflated.

FIG. 7 shows dilatation occurring without a sheath being present on the catheter shaft, as where the dilatation catheter has been initially introduced into the body lumen without a sheath. However, to reduce the steps and time between body lumen dilatation and stent deployment, the sheath could be positioned on the catheter shaft during a dilatation procedure, but with the distal portion bearing the stent kept proximal of the dilatation balloon. Moreover, the dilatation catheter shaft may be initially introduced into the body lumen with or without the sheath. If the dilatation catheter shaft is initially introduced into the body lumen without the sheath, the sheath can be subsequently introduced over the catheter shaft by removing the detachable proximal hub, advancing the sheath over the catheter shaft, and the reattaching the detachable proximal hub. The sheath can thus be introduced into the body lumen after the catheter shaft has been introduced, and even after dilatation has occurred.

In FIG. 8, the blockage 76 has been dilated and the dilatation balloon 22 has been deflated. The detachable proximal hub 16 has been removed from the catheter shaft 15 to allow a sheath 28, including a selected stent 12, to be slidably introduced and distally advanced over the catheter shaft proximal end 19.

Referring now to FIG. 9, when the sheath proximal end 32 is distal (forward) of the shaft proximal end 19, the detachable proximal hub 16 can be reattached to the catheter shaft 15. The sheath 28 is slidably advanced over the catheter 14 by maneuvering the sheath proximal end 32 until the stent 12 is positioned over the dilatation balloon 22. The slidable advancement of the sheath 28 may be achieved by the user, such as a cardiologist, grasping the sheath proximal end 32 and pushing the sheath 28 forward (distally) along the catheter shaft 15. Because the sheath proximal portion 36 preferably consists of a generally stiffer material that is resistant to longitudinal compressive forces, the user pushing on the sheath proximal end 32 causes the sheath 28 to slide over the catheter shaft 15 so that the distal portion of the sheath 34, including the stent 12, advances over the dilatation balloon 22.

After the catheter detachable proximal hub 16 has been reattached to the catheter shaft 15 and the stent 12 has been positioned over the expandable dilatation balloon, as shown in FIG. 10, the dilatation balloon 22 is expanded. The outward pressure from the dilatation balloon 22 causes the sheath proximal portion 36 to expand outwardly, which in turn forces the stent 12 to expand outwardly until the stent assumes its deployed outer diameter 60b. In the deployed diameter, the stent outer surface 58 contacts and exerts some outward pressure against the walls 82 of the body lumen 72, thereby preventing the walls 82, which may be weakened from the dilatation procedure, or the blockage 76, from collapsing inwardly and causing renewed blockage of the body lumen 72.

After the stent 12 is deployed, the detachable proximal hub 16 can be removed from the catheter shaft proximal end 19, as was shown in FIG. 8. The sheath 28 can then be slidably removed proximally from the catheter shaft 15 by the user grasping and pulling the sheath proximal end 32, so that the sheath 28 passes over the catheter shaft proximal end 19 while the catheter shaft 15 remains in place in the patient. Next, a new sheath with a new stent or stents can be loaded onto the catheter shaft, the detachable proximal hub can be reattached, the sheath slid forward until the stent(s) is over the dilatation balloon, and the dilatation balloon expanded to deploy the stent(s). (In the alternative, new stents may be loaded onto the original sheath, and the "reloaded" original sheath reintroduced over the catheter shaft 15 into the patient.) These steps can be repeated to deploy multiple stents from multiple sheaths, without necessitating removal of the catheter shaft until the procedure is completed.

FIGS. 1, 4, and 8–10 show a single stent 12 mounted on the sheath 28. However, as described in concurrently-filed U.S. Ser. No. 08/840,487, entitled SHEATH AND METHOD FOR A STENT DELIVERY SYSTEM, another embodiment of a sheath compatible with the current invention involves multiple stents mounted on a single sheath. Thus, a single sheath may be used to deploy multiple stents in a body lumen during a single procedure, without the need for the sheath to be removed from the body lumen until a plurality of stents have been deployed.

Figure 11A:
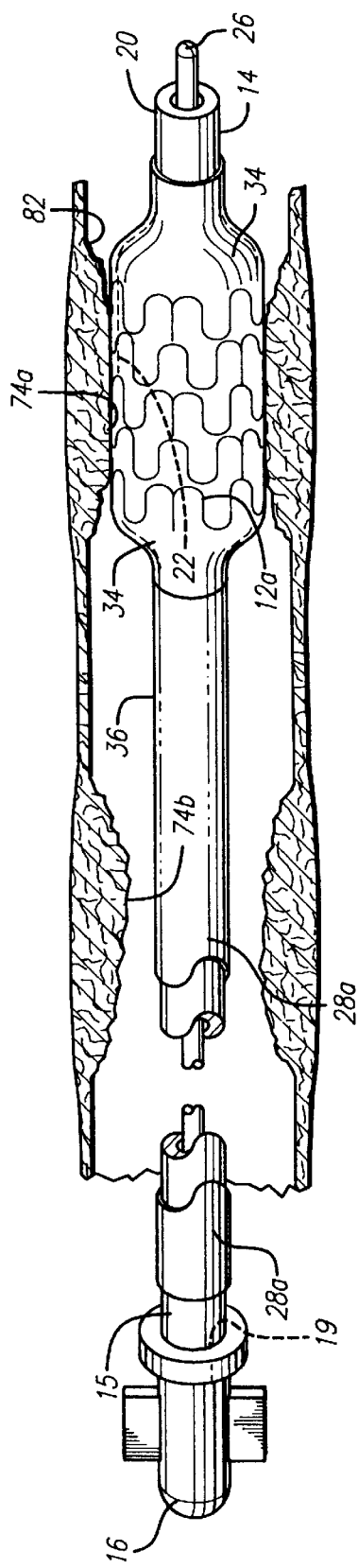
FIG. 11a is a perspective view depicting a delivery catheter, sheath, and stent assembly with the balloon expanded to deploy a first stent in a body lumen.

FIGS. 12a–12b show the catheter 14 used to deploy multiple stents in a body lumen during a single procedure, without the need for the catheter shaft 15 to be removed from the body lumen until the procedure is completed. In one method, the locations 74a, 74b to be treated may all be dilated by the dilatation balloon 22 prior to deployment of any of the stents 12. After all locations to be treated have been dilated, the deflated dilatation balloon 22 is positioned at the location 74a where the first stent 12a is to be deployed. The first sheath 28a is slidably advanced over the catheter shaft 15 until the first stent 12a is positioned over the deflated dilatation balloon 22. Then the dilatation balloon is expanded, thereby deploying the first stent 12a as shown in FIG. 11a. The dilatation balloon 22 is then deflated. The detachable proximal hub 16 is removed from the catheter shaft 15, and the first sheath 28a is removed from the catheter shaft 15.

Figure 11B:
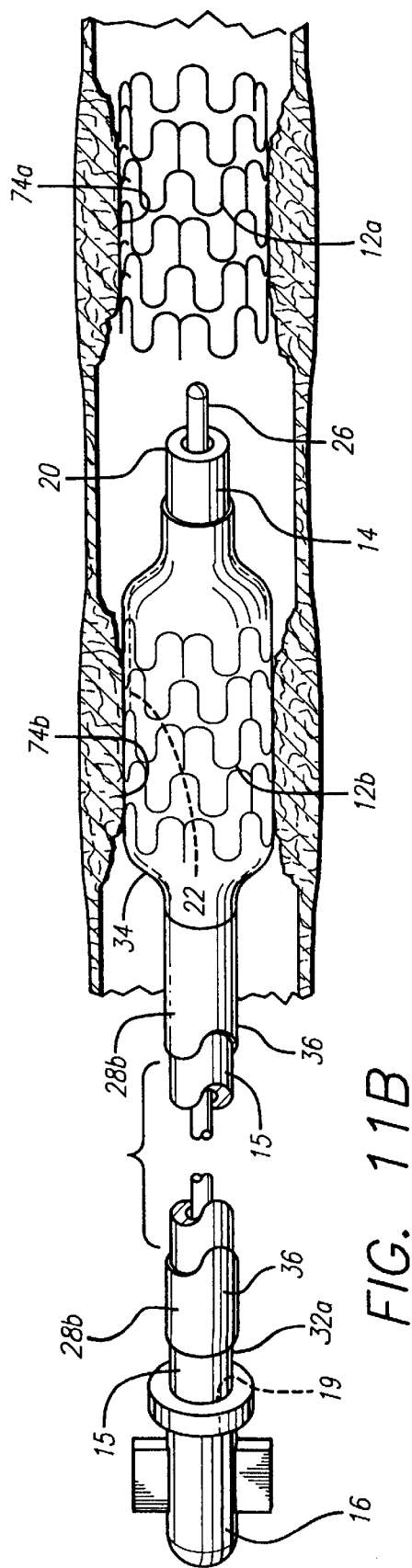
FIG. 11b is a perspective view depicting a delivery catheter, sheath, and stent assembly of FIG. 11a, with the balloon expanded to deploy a second stent in the body lumen.

The dilatation balloon is repositioned at the location 74b where a second stent 12b is to be deployed. A new sheath 28b, including the new stent 12b, is slidably advanced over the catheter shaft 15 until the sheath proximal end 32a is distal of the catheter shaft proximal end 19. The detachable proximal hub 16 is reattached to the catheter shaft 15, and the second sheath 28b is distally advanced over the catheter shaft 15 until the second stent 12b is positioned over the deflated dilatation balloon 22. The dilatation balloon is expanded to deploy the second stent 12b, as shown in FIG. 11b. The procedure is repeated for any further stents.

In another method, dilatation of selected treatment sights 74a, 74b may occur just prior to deployment of each stent, so that the first site 74a is dilated prior to deployment of the first stent 12a, followed by removal of the first sheath 28a. The second site 74b is dilated after deployment of the first stent 12a and removal of the first sheath 28a, but before the introduction of the second sheath 28b and deployment of the second stent 12b, etc.

Various embodiments of securing the removable proximal hub to the catheter shaft are applicable to the invention. For example, in the embodiment shown in FIG. 12, a catheter 14 has a proximal hub 16 including several projections 86 extending distally from the distal end 84 of the proximal hub. The shaft proximal end 19 includes corresponding apertures 88 sized and configured to slidably receive the proximal hub projections 86. The apertures 88 may be formed through various methods, such as insert molding. When the proximal hub 16 is removably secured to the shaft proximal end 19, the projections 86 lie within the apertures 88, thereby preventing axial rotation of the detachable proximal hub 16 about the catheter shaft 15. In another embodiment, projections may be located on the shaft proximal end, with corresponding apertures located on the detachable proximal hub.

Figure 13B:
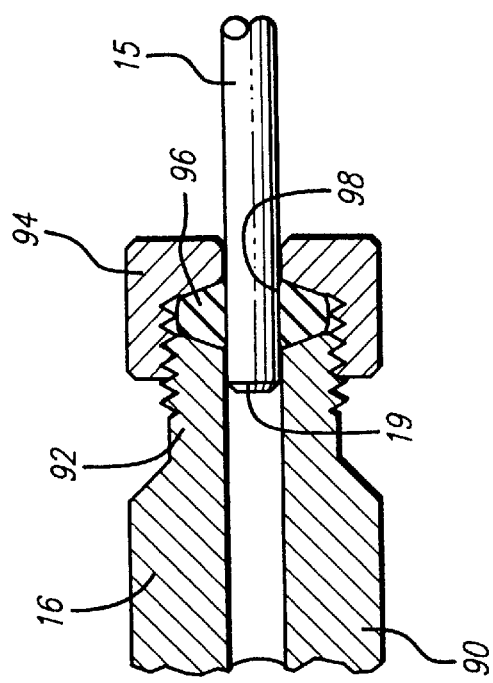
Figure 12:
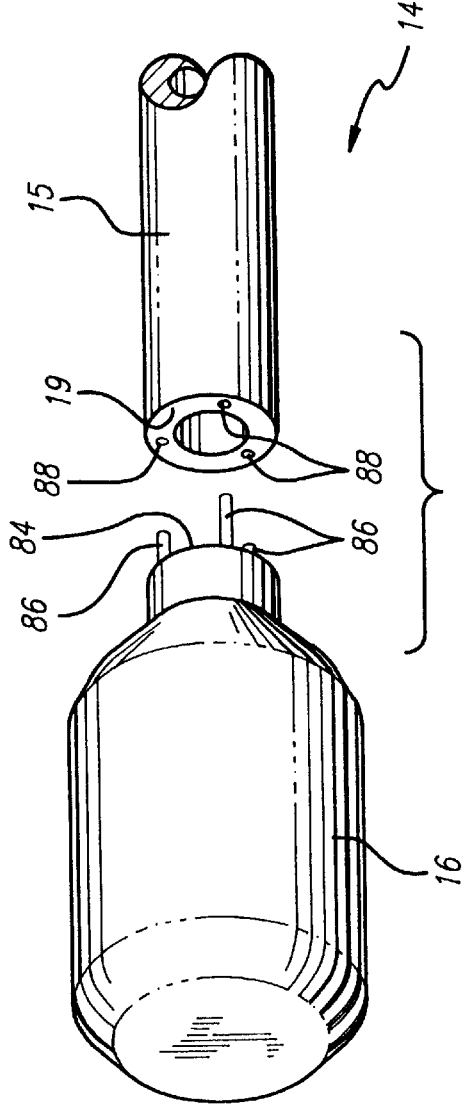
FIG. 12 is an exploded perspective view of the proximal portion of a catheter according to a preferred embodiment of the current invention.
Figure 13A:
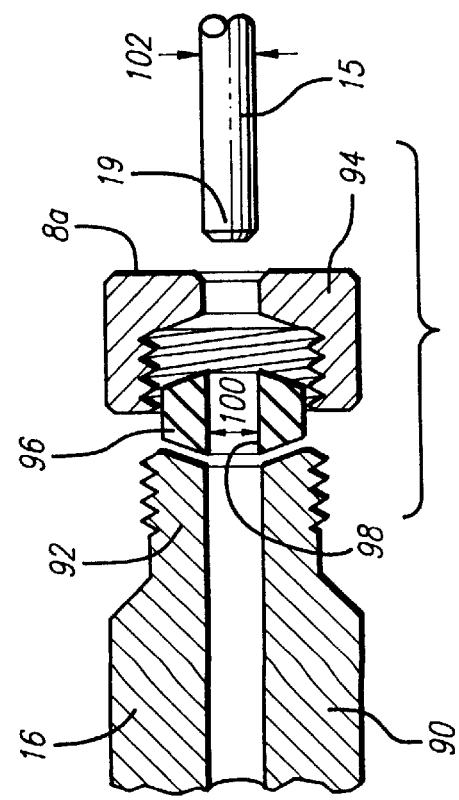
FIG. 13a is an exploded cross-sectional view of a proximal portion of a delivery catheter according to one embodiment of the invention.

Another embodiment of the catheter is shown in FIG. 13a, wherein the detachable proximal hub 16 has a base element 90 with a threaded element 92 at its distal end 84. The proximal hub 16 also includes a nose cap 94 configured to threadably receive the threaded element 92, and a compression fitting 96 positioned between the threaded element 92 and nose cap 94. The nose cap 94 and compression fitting 96 each has a central bore 98 therethrough with an inner diameter 100 sized to receive the catheter shaft proximal end outer diameter 102, as shown in FIG. 13b.

When the nose cap 94 is threadably tightened onto the threaded element 92, the compression fitting 96 presses inwardly against the catheter shaft 15. The compression fitting 96 may be formed of a compressible material, such asurethane, rubber or any plastic material which recovers after deforation, that also serves to create a seal about the catheter shaft proximal end 19 when compressed.

FIG. 14 illustrates another embodiment of the invention, wherein the catheter has an inner member 104 and outer member 106, such as is typical of over-the-wire catheters. The catheter proximal hub 16 has an inner bore 98 therethrough, with a bore distal diameter 100a configured to receive the catheter outer member 106 with a diameter 102a, and a bore proximal diameter 100b configured to receive the catheter inner member 104 with a diameter 102b.

In the embodiment of FIG. 14, the base element 90 has a first threaded element 92a configured to threadably receive a first nose cap 94a, with a first compression fitting 96a positioned between the first threaded element 92a and first nose cap 94a. The base element 90 also has a second threaded element 92b configured to threadably receive a second nose cap 94b, with a second compression fitting 96b positioned between the second threaded element 92b and second nose cap 94b.

In the embodiment of FIG. 14, the first threaded element 92a is located at the distal end 108 of the proximal hub base element 90, and the second threaded element 92b is located at the proximal end 110 of the proximal hub base element 90. The shaft inner member 104 extends proximal of the shaft outer member 106.

With the catheter shaft inner member 104 positioned inside the second compression fitting 96b, the second nose cap 94b is threadably tightened onto the second threaded element 92b, thereby compressing the second compression fitting 96b inwardly against the inner member 104. Thus, the second compression fitting 96b secures the inner member 104 while also providing a seal about the inner member 104. Similarly, the catheter shaft outer member 106 is positioned inside the first compression fitting 96a, the first nose cap 94a is threadably tightened onto the first threaded element 92a, and the first compression fitting 96a presses inwardly against the outer member 106.

FIG. 15a illustrates a further embodiment of the invention, wherein the proximal hub 16 is secured to the catheter shaft 15 via inwardly-facing projections or barbs 112. The base element 90 of the proximal hub 16 has a central bore 98 configured to receive the catheter shaft proximal end 19. The inwardly-facing projections 112 are located inside the central bore 98. The shaft may have corresponding apertures 114 sized to receive the inwardly-facing projections 112.

When the catheter shaft proximal end 19 is slid into the base element central bore 98, the inwardly-facing projections 112 engage against the outer surface 116 of the catheter shaft 15. Where corresponding apertures 114 are present on the catheter shaft 15, the inwardly-facing projections 112 are positioned in the apertures 114, thereby securing the proximal hub 16 to the catheter shaft 15.

The projections 112 may comprise one or more separate projections. Alternatively, the projections 112 may comprise a single, continuous annular ring about the central bore 98. The projections 112 may comprise a deformable material that compresses against the catheter shaft 15. Depending on the shape and configuration of the projections 112, the projections may serve to seal the seam between the catheter shaft 15 and proximal hub 16.

As shown in FIG. 15b, the catheter 14 may also include a collar 118 that strengthens the connection and seal between the proximal hub 16 and the catheter shaft 15. As shown in FIG. 16, the collar 118 may be located on the base element 90 and, when slidably or rotatably advanced into position, compresses the central bore 98, which may include projections 112, onto the catheter shaft 15. Alternatively, the collar 118 could be located on the catheter shaft 15, such as where the catheter shaft 15 fits around the distal end of the proximal hub 16 as shown in FIG. 16.

Various alternate configurations of projections and/or apertures may be used to secure the proximal hub 16 to the catheter shaft 15. For example, the catheter shaft 15 may be equipped with outward-facing projections 120, as shown in FIG. 15c. These projections may align with and engage against inwardly-facing projections 112 and/or apertures 122 in the proximal hub central bore 98.

FIG. 16a shows an alternative configuration of the invention, wherein the catheter has an inner member 104 and outer member 106, such as is typical of over-the-wire catheters. The catheter proximal hub 16 has an inner bore 98 therethrough, with an inner bore distal diameter 100a configured to receive the catheter outer member 106 with a diameter 102a, and an inner bore proximal diameter 100b configured to receive the catheter inner member 104 with a diameter 102*b*. The central bore 98 has a first set of projections 112*a* configured to engage the catheter shaft outer member 106, and a second set of projections 112*b* configured to engage the catheter shaft inner member 104.

FIG. 16*a* shows a catheter shaft having two coaxial members, i.e., and inner and an outer member. However, as shown in FIG. 16*b*, the catheter shaft may comprise two adjacent members 122, 124 in a side-by-side configuration. In the embodiment of FIG. 16*c*, the first catheter member 122 is an inflation lumen, and the second catheter member 124 is a guidewire lumen. The proximal hub 16 has two bores 126, 128. The first bore 126 is sized to receive the first catheter member 122, and the second bore 128 is sized to receive the second catheter member 124.

FIG. 17*a* depicts a proximal hub 16 having a distal end 108 sized to be received within the catheter shaft inner lumen 130. The proximal hub distal end 108 may have one or more outwardly-facing projections or barbs 132. The projection 132 may comprise a single, continuous annular ring about the proximal hub distal end 108.

When the proximal hub distal end 108 is inserted into the catheter shaft inner lumen 130, the projection 132 engages the catheter shaft inner surface 134, thereby securing the proximal hub 16 to the catheter shaft 15. The projection 132 may also serve to seal the seam between the catheter shaft 15 and proximal hub 16. The strength of the connection and seal may be improved by having inwardly-facing apertures 136 and/or projections 138 in the catheter inner surface 134. Where the catheter inner surface 134 has inwardly-facing projections 138, corresponding apertures 140 in the proximal hub distal end 108 may be used to enhance the connection and seal.

Various techniques may be used to maintain the catheter shaft 15 in position in the body lumen during the process of sliding a sheath 28 over the catheter proximal end 19 and onto the catheter shaft 15. For example, the main catheter shaft 15 may have sufficient length that, with the dilatation device properly positioned at the deployment site in the body lumen, the portion of catheter shaft that extends out of the patient 68 is of sufficient length to entirely contain the sheath 28, as shown in FIG. 18*a*. Accordingly, as a sheath 28 is being advanced or removed over the catheter shaft proximal end 19, a user can secure the catheter shaft 15 in position via a securing section 142 of the catheter shaft that is distal of the sheath 28 but still outside of the patient 68. As the sheath 28 is advanced into the body lumen and over the securing section 142, as shown in FIG. 18*b*, the user can secure the catheter shaft 15 in position via the catheter shaft proximal end 19. Accordingly, the catheter shaft 15 is secured at all times, either at the securing section 142 just outside the body lumen or via the catheter shaft proximal end 19, thereby preventing inadvertent movement of the dilatation balloon from the desired stent deployment location.

When the catheter embodiment of FIGS. 18*a* and 18*b* is used with a sheath embodiment such as that shown in FIG. 4, the catheter shaft 15 is preferably two or more times as long as the sheath length. This allows the sheath 28 to be entirely removed from the patient 68 without any portion of the sheath 28 passing over the catheter proximal end 19.

For the sheath embodiment shown in FIG. 4*a*, the catheter shaft only requires a small length to be outside of the patient due to the short length of the forward "tubular" section of the sheath 28. Unlike the proximal portion 36 of the sheath shown in FIG. 4, the mandrel 49 of the embodiment shown in FIG. 4*a* does not surround the catheter shaft 15, instead lying alongside the catheter shaft 15. Accordingly, a user can easily secure a section of the catheter shaft 15 even as the mandrel 49 is advanced alongside that section.

Another embodiment is shown in FIG. 19, whereby the catheter 14 includes a removable extender section 144 having a length 146 similar to or greater than the sheath length 52. The distal end 147 of the extender section 144 is secured to the proximal end 19 of the main catheter shaft 15. While resulting assembly of the catheter shaft 15 and extender section 144 is secured in place by a user via the extender section proximal end 148, a sheath 28 can be slid from the extender section 144 onto the main catheter shaft 15 and into proper position to deploy a stent 12 at a desired location in the body lumen. After stent deployment, a "depleted" (i.e., stentless) sheath can be slid from the main catheter shaft 15 onto the extender section 144. The extender section 144, bearing the depleted sheath, can then be removed from the main catheter shaft 15 and either discarded or reloaded with a sheath bearing a stent. During removal and replacement of the extender section 144, the catheter shaft 15 can be maintained in position via a proximal portion, such as the proximal end 19, of the main catheter shaft 15. The extender section 144 may include controls 18 that control various aspects of the catheter, such as controlling inflation of a dilatation balloon. The controls 18 may be located on a proximal hub 16 at the proximal end 148 of the extender section 144. The proximal hub 16 may be removably secured to the extender section 144.

An extender section may be provided with a sheath and stent assembly preloaded thereon, so that a user can select an extender section having a desired sheath and stent assembly, secure the extender section to the proximal end of the catheter shaft, advance the sheath over the catheter shaft until the stent is positioned at the desired location in the body lumen, and deploy the stent. The sheath can be then be slid off of the main catheter shaft and back onto the extender section. The extender section can then be replaced with another preloaded extender section containing a sheath with a stent thereon. The process can be repeated to deploy several stents in the patient without requiring removal of the main catheter shaft from the patient until the procedure is completed.

The disclosed embodiments have described the sheath and stent assembly being used with a catheter having an inflatable balloon for deployment of the stent. However, the invention is not limited to the use of expandable balloons. Other expandable devices for lumen dilatation and stent deployment are also compatible with the invention.

Although preferred and alternative embodiments of the invention have been described and illustrated, the invention is susceptible to modifications and adaptations within the ability of those skilled in the art and without the exercise of inventive faculty. Thus, it should be understood that various changes in form, detail, and usage of the present invention may be made without departing from the spirit and scope of the invention. Accordingly, it is not intended that the invention be limited, except as by the appended claims.

What is claimed is:

1. A method for deploying one or more stents in a body lumen, the method comprising the steps of:

(a) introducing a catheter shaft into a body lumen;

(b) positioning a first stent about a distal end portion of a first tubular sheath, the first stent being configured in a delivery configuration;

(c) slidably passing the first tubular sheath over a proximal end of the catheter shaft, thereby introducing the first tubular sheath into the body lumen;

(d) positioning the first stent at a first desired location within the body lumen;

(e) securing a detachable proximal hub to the proximal end of the catheter shaft; and (f) deploying the first stent at the first desired location, wherein said first stent assumes a deployed configuration.

2. The method of claim 1, including, prior to step (c) but after step (a), the further step of:

(g) removing a detachable proximal hub from a proximal end of the catheter shaft.

3. The method of claim 1, wherein the catheter includes an expandable member at the catheter shaft distal end, and wherein step (a) comprises the further step of:

(h) positioning the expandable member at the first desired position within the body lumen.

4. The method of claim 3, wherein step (d) comprises the step of:

(i) sliding the first tubular sheath over the catheter shaft until the first stent is positioned over the expandable member; and wherein step (f) includes the further step of:

(j) expanding the expandable member to deploy the first stent.

5. The method of claim 4, wherein the step of expanding the expandable member to deploy the first stent simultaneously dilates the body lumen.

6. The method of claim 3, further comprising the step of:

(k) dilating the body lumen with the expandable member.

7. The method of claim 1, comprising, after step (f), the further steps of:

(l) removing the detachable proximal hub from the catheter shaft;

(m) slidably removing the first tubular sheath from the catheter shaft;

(n) positioning a second stent about a distal end portion of a second tubular sheath, the second stent being configured in a delivery configuration;

(o) slidably passing the second tubular sheath over the proximal end of the catheter shaft, thereby introducing the second tubular sheath into the body lumen;

(p) positioning the second stent at a second desired location within the body lumen;

(q) securing the detachable proximal hub to the proximal end of the catheter shaft; and (r) deploying the second stent at the second desired location, wherein said second stent assumes a deployed configuration.

8. The method of claim 7, wherein steps (l) through (r) are repeated for additional sheaths and stents.

* * * * *

UNITED STATES PATENT AND TRADEMARK OFFICE
CERTIFICATE OF CORRECTION

PATENT NO. : 6,019,777
DATED : Feb. 1, 2000
INVENTOR(S) : Andrew James Mackenzie It is certified that error appears in the above-identified patent and that said Letters Patent is hereby corrected as shown below:

Title page, under OTHER PUBLICATIONS, add the following:
 --Palmez, et al., Expandable Intraluminal Graft: A
 Preliminary Study; *Radiology Journal*, pp. 73-77, 1985.
  Duprat, et al., Flexible Balloon-Expanded Stent for
 Small Vessels, *Radiology Journal*, pp. 276-278, 1987.--.

Column 9, line 49, change "deforation", to read
 --deformation--.

Signed and Sealed this

Twentieth Day of February, 2001

Attest:

NICHOLAS P. GODICI

*Attesting Officer*  Acting Director of the United States Patent and Trademark Office